United States Patent [19]

Grese

[11] Patent Number: 5,446,071
[45] Date of Patent: Aug. 29, 1995

[54] METHODS FOR LOWERING SERUM CHOLESTEROL

[75] Inventor: Timothy A. Grese, Indianapolis, Ind.

[73] Assignee: Eli Lilly and Company, Indianapolis, Ind.

[21] Appl. No.: 342,181

[22] Filed: Nov. 18, 1994

[51] Int. Cl.$^6$ .................. A61K 31/00; A61K 31/44
[52] U.S. Cl. .................. 514/307; 514/309; 514/310; 514/824; 514/312; 514/313; 514/314; 514/324; 514/320; 514/319
[58] Field of Search .............. 514/307, 309, 310, 824

[56] References Cited

U.S. PATENT DOCUMENTS

| | | | |
|---|---|---|---|
| 3,870,722 | 3/1975 | Houlihan et al. | 546/144 |
| 3,914,236 | 10/1975 | Lerch et al. | 546/143 |
| 3,961,062 | 6/1976 | Lerch et al. | 514/310 |
| 4,447,662 | 5/1984 | Salman et al. | 548/525 |
| 5,362,878 | 11/1994 | Chang et al. | 546/296 |

FOREIGN PATENT DOCUMENTS

WO93/1074  6/1993  WIPO .

*Primary Examiner*—Arthur C. Prescott
*Attorney, Agent, or Firm*—Steven A. Fontana; David E. Boone; Gerald V. Dahling

[57] ABSTRACT

The present invention provides methods for lowering serum cholesterol comprising administering to a mammal in need of treatment a serum cholesterol lowering amount of a compound of formula I or formula II

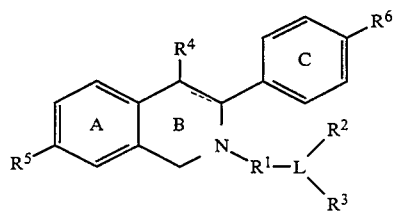

wherein
L is —CON< or —N<; and
the dotted line in the B-ring is an optional bond; or a pharmaceutically acceptable salt thereof; and

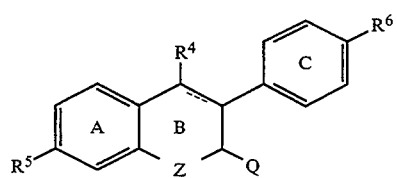

wherein
Q is a moiety having the formula

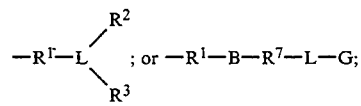

L is —CON< or —N<;
B is —O—, —S—, —CH$_2$-phenyl-O—, -phenyl-O—, or -benzyl-O—;
G is a moiety which together with L forms a substituted or unsubstituted heterocyclic ring having at least one nitrogen atom or is selected from the group consisting of hydrogen, lower alkyl, lower alkenyl, lower alkynyl, (C$_3$-C$_7$)cycloalkyl, halo(lower)alkyl, cyano(lower)alkyl, carboxy(lower)alkyl, (lower)alkoxycarbonyl(lower)alkyl, (C$_6$-C$_{10}$)aryl, (C$_7$-C$_{11}$)aryl akyl, di(lower)alkylamino(lower)alkyl, and fluoro-substituted analogs of the foregoing;
Z is —O—, —S—, —CH$_2$—, —NH—; or —N(CH$_3$)—; and
the dotted line in the B-ring is an optional bond; or a pharmaceutically acceptable salt thereof.

21 Claims, No Drawings

METHODS FOR LOWERING SERUM CHOLESTEROL

BACKGROUND OF THE INVENTION

All mammalian cells require cholesterol as a structural component of their cell membranes and for non-sterol end products. The very property, however, that makes cholesterol useful in the cell membranes, its insolubility in water, also makes it potentially lethal. When cholesterol accumulates in the wrong place, for example within the wall of an artery, it cannot be readily mobilized and its presence leads to the development of an atherosclerotic plaque. Elevated concentrations of serum cholesterol associated with low density lipoproteins (LDL'S) have been demonstrated to be a major contributing factor in the development and progression of atherosclerosis.

Estrogen, particularly when taken orally, lowers plasma levels of LDL and raises those of the beneficial high density lipoproteins (HDL's). Long-term estrogen therapy, however, has been implicated in a variety of disorders, including an increase in the risk of uterine cancer and possibly breast cancer, causing many women to avoid this treatment. Recently suggested therapeutic regimens, which seek to lessen the cancer risk, such as administering combinations of progestogen and estrogen, cause the patient to experience unacceptable bleeding. Furthermore, combining progesterone with estrogen seems to blunt the serum cholesterol lowering effects of estrogen. The significant undesirable effects associated with estrogen therapy support the need to develop alternative therapies for hypercholesterolemia that have the desirable effect on serum LDL but do not cause undesirable effects.

Attempts to fill this need by the use of compounds commonly known as antiestrogens, which interact with the estrogen receptor and/or bind what has been termed the antiestrogen binding site (AEBS), have had limited success, perhaps due to the fact that these compounds generally display a mixed agonist/antagonist effect and are subject to the same adverse effects associated with estrogen therapy.

SUMMARY OF THE INVENTION

The present invention provides a method for lowering serum cholesterol comprising administering to a mammal in need of treatment a cholesterol lowering amount of a compound of formula I

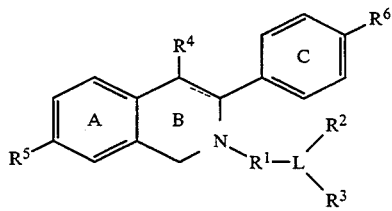

wherein
$R^1$ is —H or is a bivalent moiety which distances L from the B-ring by 6–8 intervening atoms;
$R^2$ is —H or selected from the group consisting of hydrogen, a straight or branched, saturated or unsaturated chain having 1–5 carbon atoms, a substituted or unsubstituted cycloalkyl group having 5–7 carbon atoms, a bivalent moiety which joins $R^3$ and L to form a 5- to 7-membered heterocyclic ring, and halo-substituted derivatives of the foregoing;
$R^3$ is absent or selected from the group consisting of hydrogen, a straight or branched, saturated or unsaturated chain having 1–5 carbon atoms, a substituted or unsubstituted bivalent moiety which joins $R^2$ and L to form a 5- to 7-membered heterocyclic ring, and halo-substituted derivatives of the foregoing;
$R^4$ is hydrogen or lower alkyl;
$R^5$ and $R^6$ each are independently hydrogen, hydroxy, or a moiety which is converted to hydroxy in vivo;
L is —CON< or —N<; and
the dotted line in the B-ring is an optional bond; or a pharmaceutically acceptable salt thereof.

The present invention further provides a method for lowering serum cholesterol comprising administering to a mammal in need of treatment a cholesterol lowering amount of a compound of formula II

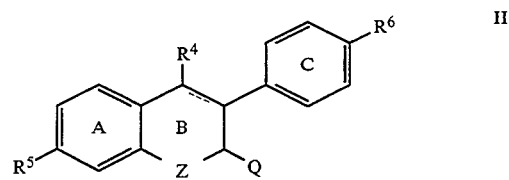

wherein
Q is a moiety having the formula

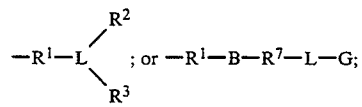

$R^1$ is absent or is a bivalent moiety which distances L from the B-ring by 6–8 intervening atoms;
$R^2$ is absent or selected from the group consisting of hydrogen, a straight or branched, saturated or unsaturated chain having 1–5 carbon atoms, a substituted or unsubstituted cycloalkyl group having 5–7 carbon atoms, a bivalent moiety which joins $R^3$ and L to form a 5- to 7-membered heterocyclic ring, and halo-substituted derivatives of the foregoing;
$R^3$ is absent or selected from the group consisting of hydrogen, a straight or branched, saturated or unsaturated chain having 1–5 carbon atoms, a substituted or unsubstituted bivalent moiety which joins $R^2$ and L to form a 5- to 7-membered heterocyclic ring, and halo-substituted derivatives of the foregoing;
L is —CON< or —N<;
B is —O—, —S—, —CH$_2$-phenyl-O—, -phenyl-O—, or -benzyl-O—;
$R^7$ is absent or selected from the group consisting of straight- or branched-chain alkylene, straight- or branched-chain alkenylene, phenylene, and fluoro-substituted analogs of the foregoing;
G is a moiety which together with L forms a substituted or unsubstituted heterocyclic ring having at least one nitrogen atom or is selected from the group consisting of hydrogen, lower alkyl, lower alkenyl, lower alkynyl, (C$_3$–C$_7$)cycloalkyl, halo(lower)alkyl, cyano(lower)alkyl, carboxy(lower)alkyl, (lower)alkoxycarbonyl(lower)alkyl, (C$_6$–C$_1$- o)aryl, (C$_7$-C$_{11}$)aryl akyl, di(lower)alkylamino(lower)alkyl, and fluoro-substituted analogs of the foregoing;

R$^4$ is hydrogen or lower alkyl;

R$^5$ and R$^6$ each are independently hydrogen, hydroxy, or a moiety which is converted to hydroxy in vivo;

Z is —O—, —S—, —CH$_2$—, —NH—; or —N(CH$_3$)—; and the dotted line in the B-ring is an optional bond; or a pharmaceutically acceptable salt thereof.

DETAILED DESCRIPTION OF THE INVENTION

The present invention relates to methods for lowering serum cholesterol comprising administering to a mammal a serum cholesterol lowering amount of a compound of formula I or formula II

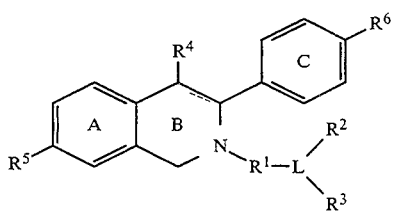

wherein

R$^1$ is —H or is a bivalent moiety which distances L from the B-ring by 6–8 intervening atoms;

R$^2$ is —H or selected from the group consisting of hydrogen, a straight or branched, saturated or unsaturated chain having 1–5 carbon atoms, a substituted or unsubstituted cycloalkyl group having 5–7 carbon atoms, a bivalent moiety which joins R$^3$ and L to form a 5- to 7-membered heterocyclic ring, and halo-substituted derivatives of the foregoing;

R$^3$ is absent or selected from the group consisting of hydrogen, a straight or branched, saturated or unsaturated chain having 1–5 carbon atoms, a substituted or unsubstituted bivalent moiety which joins R$^2$ and L to form a 5- to 7-membered heterocyclic ring, and halo-substituted derivatives of the foregoing;

R$^4$ is hydrogen or lower alkyl;

R$^5$ and R$^6$ each are independently hydrogen, hydroxy, or a moiety which is converted to hydroxy in vivo;

L is —CON< or —N<; and the dotted line in the B-ring is an optional bond; or a pharmaceutically acceptable salt thereof; and

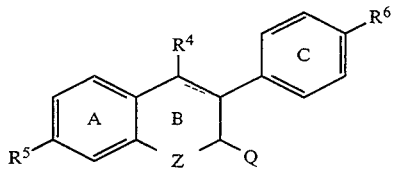

wherein

Q is a moiety having the formula

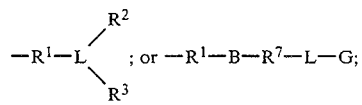

R$^1$ is absent or is a bivalent moiety which distances L from the B-ring by 6–8 intervening atoms;

R$^2$ is absent or selected from the group consisting of hydrogen, a straight or branched, saturated or unsaturated chain having 1–5 carbon atoms, a substituted or unsubstituted cycloalkyl group having 5–7 carbon atoms, a bivalent moiety which joins R$^3$ and L to form a 5- to 7-membered heterocyclic ring, and halo-substituted derivatives of the foregoing;

R$^3$ is absent or selected from the group consisting of hydrogen, a straight or branched, saturated or unsaturated chain having 1–5 carbon atoms, a substituted or unsubstituted bivalent moiety which joins R$^2$ and L to form a 5- to 7-membered heterocyclic ring, and halo-substituted derivatives of the foregoing;

L is —CON< or —N<;

B is —O—, —S—, —CH$_2$-phenyl-O—, -phenyl-O—, or -benzyl-O—;

R$^7$ is absent or selected from the group consisting of straight- or branched-chain alkylene, straight- or branched-chain alkenylene, phenylene, and fluoro-substituted analogs of the foregoing;

G is a moiety which together with L forms a substituted or unsubstituted heterocyclic ring having at least one nitrogen atom or is selected from the group consisting of hydrogen, lower alkyl, lower alkenyl, lower alkynyl, (C$_3$-C$_7$) cycloalkyl, halo(lower)alkyl, cyano(lower)alkyl, carboxy(lower)alkyl, (lower)alkoxycarbonyl(lower)alkyl, (C$_6$-C$_{10}$)aryl, (C$_7$-C$_{11}$)aryl akyl, di(lower)alkylamino(lower)alkyl, and fluoro-substituted analogs of the foregoing;

R$^4$ is hydrogen or lower alkyl;

R$^5$ and R$^6$ each are independently hydrogen, hydroxy, or a moiety which is converted to hydroxy in vivo;

Z is —O—, —S—, —CH$_2$—, —NH—; or —N(CH$_3$)—; and the dotted line in the B-ring is an optional bond; or a pharmaceutically acceptable salt thereof.

The present invention concerns the discovery that the compounds of formulae I and II are useful for lowering serum cholesterol. The methods of treatment provided by this invention can be practiced by administering to an animal an amount that lowers serum cholesterol of a compound of formula I or formula II, or a pharmaceutically acceptable salt thereof. The methods include both medical therapeutic and/or prophylactic treatment, as appropriate. Generally, a formula I or formula II compound is formulated with common excipients, diluents or carriers, and put into capsules or compressed into tablets, or formulated as elixirs or solutions for convenient oral administration, or administered by intramuscular or intravenous routes. The compounds may also be administered transdermally.

The methods of this invention also include the administration of a compound of formula I or formula II together with estrogen, either independently or in combination. The term estrogen as used herein refers to any compound which approximates the spectrum of activities of the naturally acting molecule which is commonly believed to be 17β-estradiol. Examples of such compounds include estriol, estrone, ethynyl estradiol, Premarin ® (a commercial preparation of conjugated estrogens isolated from natural sources-Ayerst), and the like.

All of the compounds used in the methods of the present invention can be made according to established or analogous procedures, such as those detailed in PCT Application WO 93/10741. Modifications to these methods may be necessary to accommodate reactive functionalities of particular substituents. Such modifications would be either apparent to, or readily ascertained by, those skilled in the art.

Preferred formula I compounds are those in which L is —N< and $R^2$ joins with $R^3$ and L to form a 5- to 7-membered heterocyclic ring, particularly piperidino.

Preferred formula II compounds are those in which
$R^1$ is -H;
$R^4$ is lower alkyl;
B is -phenyl-O— or —$CH_2$-benzyl-O—;
$R^7$ is $(CH_2)_2$;
Z is —$CH_2$—;
the dotted line in the B-ring is a bond;
Q is a moiety having a formula $R^1$—B—$R^7$—L—G;
L is —N<; and
G is a moiety which together with L forms a heterocyclic ring, particularly piperidino. Of these, formula II compounds in which $R^4$ is methyl and $R^5$ is —H and $R^6$ is hydroxy are especially preferred.

Other preferred formula II compounds include those in which
$R^1$ is —$(CH_2)_6$—;
the dotted line in the B-ring is a bond;
Q is a moiety having the formula

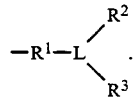

L is —N<;
$R^2$ joins $R^3$ and L to form a 5- to 7-membered heterocyclic ring, especially piperidino;
$R^4$ is lower alkyl; and
Z is —O—. Of these, formula II compounds in which $R^4$ is methyl and $R^5$ and $R^6$ are hydroxy are especially preferred.

The formula I and formula II compounds used in the methods of the present invention can form pharmaceutically acceptable acid and base addition salts with a variety of organic and inorganic acids and bases and include the physiologially acceptable salts which are often used in pharmaceutical chemistry. Such salts are also part of this invention. Typical inorganic acids used to form such salts include hydrochloric, hydrobromic, hydroiodic, nitric, sulfuric, phosphoric, hypophosphoric and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, β-hydroxybutyrate, butyne-1,4-dioate, hexyne-1,4-dioate, caprate, caprylate, chloride, cinnamate, citrate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzene-sulfonate, p-bromophenylsulfonate, chlorobenzene-sulfonate, ethanesulfonate, 2-hydroxyethanesulfonate, methane-sulfonate, naphthalene-1-sulfonate, naphthalene-2-sulfonate, p-toluenesulfonate, xylenesulfonate, tartrate, and the like.

The pharmaceutically acceptable acid addition salts are typically formed by reacting a compound of formula I or formula II with an equimolar or excess amount of acid. The reactants are generally combined in a mutual solvent such as diethyl ether or benzene. The salt normally precipitates out of solution within about one hour to 10 days and can be isolated by filtration or the solvent can be stripped off by conventional means.

Bases commonly used for formation of salts include ammonium hydroxide and alkali and alkaline earth metal hydroxides, carbonates and bicarbonates, as well as aliphatic and aromatic amines, aliphatic diamines and hydroxy alkylamines. Bases especially useful in the preparation of addition salts include ammonium hydroxide, potassium carbonate, sodium bicarbonate, calcium hydroxide, methylamine, diethylamine, ethylene diamine, cyclohexylamine and ethanolamine.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, a formula I or formula II compound, either alone or in combination with estrogen, can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinylpyrrolidone; moisturizing agents such as glycerol; disintegrating agents such as agaragar, calcium carbonate, and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

Compounds of formula I and II, either alone or in combination with estrogen, can also be formulated as elixirs or solutions for convenient oral administration or as solutions appropriate for parenteral administration, for instance by intramuscular, subcutaneous or intravenous routes. Additionally, the compounds, either alone or in combination with estrogen, can be formulated as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I or formula II required to lower serum cholesterol according to this invention will depend upon the severity of the condition, the route of administration, and related factors. In humans, generally accepted and effective daily doses will be from about 0.1 to about 1000 mg, and more typically from about 50 to about 600 mg. Such dosages will be administered to the patient from once to about three times each day, or more often as needed to lower serum cholesterol effectively.

If estrogen is also administered, generally accepted and effective daily doses of estrogen will be from about 0.01 to about 4.0 mg, and more typically from about 0.1 to about 2.0 mg. These doses are also administered to the patient from once to about three times a day, or more often as needed.

For the purposes of this invention, the following are typical oral dosage forms. In these examples, "Active ingredient" means a compound of formula I or formula II.

Capsules

Formulation 1:

Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

Tablets

The components in Formulation I can be blended and compressed to form tablets.

Alternatively, tablets each containing 0.1–1000 mg of active ingredient are made up as follows:
Formulation 2:

| Ingredient | Quantity (mg/tablet) |
| --- | --- |
| Active ingredient | 0.1–1000 |
| Starch | 45 |
| Cellulose, microcrystalline | 35 |
| Polyvinylpyrrolidone | 4 |
| (as 10% solution in water) | |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions

Suspensions each containing 0.1–1000 mg of medicament per 5 mL dose are made as follows:
Formulation 3:

| Ingredient | Quantity (amount/5 mL) |
| --- | --- |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water | qs to 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.
Formulation 4:

| Ingredient | Quantity (mg/capsule) |
| --- | --- |
| Active ingredient | 50 |
| Premarin | 1 |
| Avicel pH 101 | 50 |
| Starch 1500 | 117.50 |
| Silicon Oil | 2 |
| Tween 80 | 0.50 |
| Cab-O-Sil | 0.25 |

Formulation 5:
Combination Capsule II

| Ingredient | Quantity (mg/capsule) |
| --- | --- |
| Active ingredient | 50 |
| Norethylnodrel | 5 |
| Avicel pH 101 | 82.50 |
| Starch 1500 | 90 |
| Silicon Oil | 2 |
| Tween 80 | 0.50 |

Formulation 6:
Combination Tablet

| Ingredient | Quantity (mg/capsule) |
| --- | --- |
| Active ingredient | 50 |
| Premarin | 1 |
| Corn Starch NF | 50 |
| Povidone, K29-32 | 6 |
| Avicel pH 101 | 41.50 |
| Avicel pH 102 | 136.50 |
| Crospovidone XL10 | 2.50 |
| Magnesium Stearate | 0.50 |
| Cab-O-Sil | 0.50 |

The following nonlimiting test examples illustrate the methods of this invention.
Test Procedures Seventy-five day old female Sprague Dawley rats (weight range of 200 to 225 g) are obtained from Charles River Laboratories (Portage, Mich.). The animals are either bilaterally ovariectomized (OVX) or exposed to a Sham surgical procedure at Charles River Laboratories, and then shipped after one week. Upon arrival, they are housed in metal hanging cages in groups of 3 or 4 per cage and have ad libitum access to food (calcium content approximately 0.5%) and water for one week. Room temperature is maintained at 22.2°±1.7° C. with a minimum relative humidity of 40%. The photoperiod in the room is 12 hours light and 12 hours dark.

Dosing Regimen/Tissue Collection. After a one week acclimation period (therefore, two weeks post-OVX) daily dosing with test compound is initiated. All compounds are administered orally at 1 ml/kg body weight unless otherwise stated. 17α-ethynyl estradiol and the test compound are given orally as a suspension in 1% carboxymethylcellulose or 20% cyclodextrin. Animals are dosed daily for 4 days. Following the dosing regimen animals are weighed and anesthetized with a ketamine: Xylazine (2:1, V:V) mixture, and a blood sample is collected by cardiac puncture. Each animal is then sacrificed by asphyxiation with $CO_2$; the uterus is removed through a midline incision and a wet weight is determined.

Cholestrol Analysis. Blood samples are allowed to clot at room temperature for 2 hours, and serum is obtained following centrifugation for 10 minutes at 3000 rpm. Serum cholesterol is determined using a Boehringer Mannheim Diagnostics high performance cholesterol assay. Briefly, the cholesterol is oxidized to cholest-4-en-3-one and hydrogen peroxide. The hydrogen peroxide is then reacted with phenol and 4-aminophenazone in the presence of peroxidase to produce a p-quinone imine dye, which is read spectrophotemetrically at 500 nm. Cholesterol concentration is then calculated against a standard curve.

Uterine Eosinophil Peroxidase (EPO) Assay. Uteri are kept at 4° C. until time of enzymatic analysis. The uteri are then homogenized in 50 volumes of 50 mM Tris buffer (pH—8.0) containing 0.005% Triton X-100. Upon addition of 0.01% hydrogen peroxide and 10 mM o-phenylenediamine (final concentrations) in Tris buffer, increase in absorbance was monitored for 1 minute at 450 nm. The presence of eosinophils in the uterus is an indication of estrogenic activity of a compound. The maximal velocity of a 15 second interval is determined over the initial, linear portion of the reaction curve.

I claim:

1. A method for lowering serum cholesterol comprising administering to a mammal in need of treatment a cholesterol lowering amount of a compound of formula I

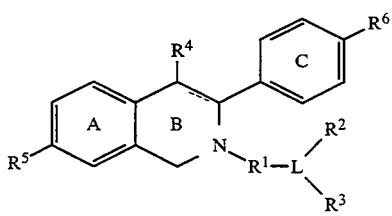

wherein $R^1$ is —H or is a bivalent moiety which distances L from the B-ring by 6–8 intervening atoms;

$R^2$ is —H or selected from the group consisting of hydrogen, a straight or branched, saturated or unsaturated chain having 1–5 carbon atoms, a substituted or unsubstituted cycloalkyl group having 5–7 carbon atoms, a bivalent moiety which joins $R^3$ and L to form a 5- to 7-membered heterocyclic ring, and halo-substituted derivatives of the foregoing;

$R^3$ is absent or selected from the group consisting of hydrogen, a straight or branched, saturated or unsaturated chain having 1–5 carbon atoms, a substituted or unsubstituted bivalent moiety which joins $R^2$ and L to form a 5- to 7-membered heterocyclic ring, and halo-substituted derivatives of the foregoing;

$R^4$ is hydrogen or lower alkyl;

$R^5$ and $R^6$ each are independently hydrogen, hydroxy, or a moiety which is converted to hydroxy in vivo;

L is —CON< or —N<; and the dotted line in the B-ring is an optional bond; or a pharmaceutically acceptable salt thereof.

2. A method according to claim 1 wherein said compound of formula I is a compound wherein L is —N<, $R^2$ joins with $R^3$ and L to form a 5- to 7-membered heterocyclic ring, and the dotted line in the B-ring is a bond.

3. A method according to claim 2 wherein said heterocyclic ring is 6-membered.

4. A method according to claim 3 wherein said mammal is a human.

5. A method for lowering serum cholesterol comprising administering to a mammal in need of treatment a cholesterol lowering amount of a compound of formula II

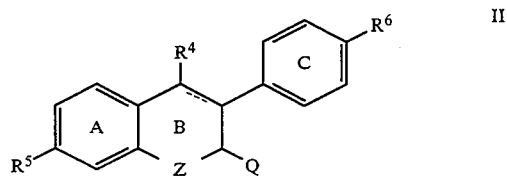

wherein

Q is a moiety having the formula

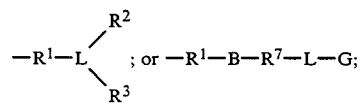

$R^1$ is absent or is a bivalent moiety which distances L from the B-ring by 6–8 intervening atoms;

$R^2$ is absent or selected from the group consisting of hydrogen, a straight or branched, saturated or unsaturated chain having 1–5 carbon atoms, a substituted or unsubstituted cycloalkyl group having 5–7 carbon atoms, a bivalent moiety which joins $R^3$ and L to form a 5- to 7-membered heterocyclic ring, and halo-substituted derivatives of the foregoing;

$R^3$ is absent or selected from the group consisting of hydrogen, a straight or branched, saturated or unsaturated chain having 1–5 carbon atoms, a substituted or unsubstituted bivalent moiety which joins $R^2$ and L to form a 5- to 7-membered heterocyclic ring, and halo-substituted derivatives of the foregoing;

L is —CON< or —N<;

B is —O—, —S—, —$CH_2$-phenyl-O—, -phenyl-O—, or -benzyl-O—;

$R^7$ is absent or selected from the group consisting of straight- or branched-chain alkylene, straight- or branched-chain alkenylene, phenylene, and fluoro-substituted analogs of the foregoing;

G is a moiety which together with L forms a substituted or unsubstituted heterocyclic ring having at least one nitrogen atom or is selected from the group consisting of hydrogen, lower alkyl, lower alkenyl, lower alkynyl, ($C_3$-$C_7$)cycloalkyl, halo(lower)alkyl, cyano(lower)alkyl, carboxy(lower)alkyl, (lower)alkoxycarbonyl(lower)alkyl, ($C_6$-$C_{10}$)aryl, ($C_7$-$C_{11}$)aryl akyl, di(lower)alkylamino(lower)alkyl, and fluoro-substituted analogs of the foregoing;

$R^4$ is hydrogen or lower alkyl;

$R^5$ and $R^6$ each are independently hydrogen, hydroxy, or a moiety which is converted to hydroxy in vivo;

Z is —O—, —S—, —$CH_2$—, —NH—; or —N($CH_3$)—; and the dotted line in the B-ring is an optional bond; or a pharmaceutically acceptable salt thereof.

6. A method according to claim wherein said mammal is a human.

7. A method according to claim 6 wherein $R^4$ is methyl, ethyl, or propyl.

8. A method according to claim 7 wherein $R^4$ is methyl.

9. A method according to claim 8 wherein Q is a moiety having the formula $R^1$—B—$R^7$—L—G.

10. A method according to claim 9 wherein
$R^1$ is absent;
B is -phenyl-O— or $CH_2$-phenyl-O—;
$R^7$ is —($CH_2$)$_2$—;
Z is —$CH_2$—;
L is —N<;
G is a moiety which together with L forms a heterocyclic ring; and
the dotted line in the B-ring is a bond; or a pharmaceutically acceptable salt thereof.

11. A method according to claim 10 wherein $R^5$ is —H and $R^6$ is hydroxy.

12. A method according to claim 11 wherein said G moiety, together with L, is piperidino.

13. A method according to claim 12 wherein B is -phenyl-O—.

14. A method according to claim 12 wherein B is —$CH_2$-phenyl-O—.

15. A method according to claim 8 wherein Q is a moiety having the formula

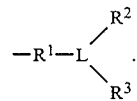

16. A method according to claim 15 wherein
$R^1$ is —($CH_2$)$_6$—;
L is —N<;
$R^2$ joins with $R^3$ and L to form a 5- to 7-membered heterocyclic ring;
Z is —O—; and
the dotted line in the B-ring is a bond; or a pharmaceutically acceptable salt thereof.

17. A method according to claim 16 wherein said 5- to 7-membered heterocyclic ring is piperidino.

18. A method according to claim 17 wherein $R^5$ and $R^6$ each are hydroxy.

19. A method according to claim 5 wherein L is —N and G is =$C_{j-1}$—$H_{2j-2}$O or =$C_jH_{2j}$, in which j is an integer from 4 to 6, or a pharmaceutically acceptable salt thereof.

20. A method for lowering serum cholesterol comprising the method of claim 1, and further comprising administering to said mammal an effective amount of estrogen.

21. A method for lowering serum cholesterol comprising the method of claim 5, and further comprising administering to said mammal an effective amount of estrogen.

* * * * *

UNITED STATES PATENT AND TRADEMARK OFFICE
CERTIFICATE OF CORRECTION

PATENT NO. : 5,446,071
DATED : August 29, 1995
INVENTOR(S) : Timothy A. Grese

It is certified that error appears in the above-indentified patent and that said Letters Patent is hereby corrected as shown below:

Claim 6, column 11, line 23, delete the term "claim wherein" and replace it with --claim 5 wherein --.

Claim 16, column 12, line 22, delete the term "Z is -O-m;" and replace it with --Z is -O-; --.

Signed and Sealed this

Twenty-third Day of January, 1996

BRUCE LEHMAN

Attest:

Attesting Officer

Commissioner of Patents and Trademarks